United States Patent [19]

Rollband

[11] Patent Number: 5,213,565
[45] Date of Patent: May 25, 1993

[54] TEMPORARY BANDAGE TAPE

[76] Inventor: Ernest J. Rollband, 3415 Slaterville Rd., Brooktondale, N.Y. 14817

[21] Appl. No.: 621,261

[22] Filed: Dec. 3, 1990

[51] Int. Cl.$^5$ ............................................. A61L 15/00
[52] U.S. Cl. ........................................ 602/41; 602/42; 602/52; 602/55; 602/58; 602/903
[58] Field of Search ............... 128/155, 156, 167, 170, 128/171; 606/215

[56] References Cited

U.S. PATENT DOCUMENTS

| | | |
|---|---|---|
| 1,643,926 | 9/1927 | Dickson ............................... 128/170 |
| 4,631,227 | 12/1986 | Nakamura . |
| 4,730,611 | 3/1988 | Lamb . |
| 4,803,078 | 2/1989 | Sakal . |
| 4,807,613 | 2/1989 | Koehnke et al. . |
| 4,837,002 | 6/1989 | Dunshee et al. ..................... 128/155 |
| 4,843,371 | 10/1955 | Grossmann et al. ................ 128/158 |
| 4,909,243 | 3/1990 | Krank et al. . |
| 4,930,500 | 6/1990 | Morgan . |

FOREIGN PATENT DOCUMENTS 1323319 7/1970 United Kingdom ............... 128/158

OTHER PUBLICATIONS

Scotch Label Protection (3M Consumer Products Group).

Primary Examiner—Randall L. Green
Assistant Examiner—K. M. Reichle
Attorney, Agent, or Firm—Barnard & Brown

[57] ABSTRACT

A tape for attaching bandages, with non-adhesive tabs at each end for easy manipulation and removal while wearing gloves, are disclosed. Also disclosed are a temporary bandage with non-adhesive ends; a roll formation of such tapes, each tape section separated from the others by a perforated section, such that it may be easily removed from the roll; and methods of forming the tapes and bandages.

2 Claims, 3 Drawing Sheets

TEMPORARY BANDAGE TAPE

BACKGROUND OF THE INVENTION

1. Field of the Invention

This invention relates to bandages and tapes, particularly that are used in a temporary fashion, such as in a hospital or dialysis situation, and to tapes which are designed for use by those wearing gloves.

2. Description of the Related Art

In the past few years, in view of increasing health risks to practitioners in all areas of medicine, the use of rubber gloves has become routine. Furthermore, temporary tapes and bandages must be removed or changed frequently during many procedures. When one is wearing rubber gloves, however, the application and removal of tapes and bandages becomes a problem. The edges of the tapes are difficult to separate from the skin with a gloved hand, and the adhesive of the tapes sticks stubbornly to the gloves. Attempts to remove the used tape from the gloves often result in tearing or stretching the glove, which can defeat the very purpose of wearing the gloves in the first place.

For example, during kidney dialysis, or when blood is donated or received, needles and tubing must be taped to the patient's arm, and then removed; a bandage must be secured over the resulting wound until there is no longer a possibility of bleeding, and then it too is removed. During these procedures, the practitioners must wear gloves, due to the possibility of contamination from blood that is infected with hepatitis, the HIV virus, or other infectious agents. With the existing bandages and tapes, these procedures are difficult to accomplish while wearing gloves.

Up to this time, most of the development in this area has been focused on the separation of the tape from the backing which is used to protect the tape until it is used. For example, U.S. Pat. No. 4,807,613 (Koehnke) discloses a bandage in which non-adhesive tabs similar to those of the present invention are presented as a means for separating the bandage from its shield. Although the tabs of that invention may also allow for easier removal of the bandage from the skin if the adhesive used is not very strong, the perforations between the tabs and the adhesive part of the bandage present an undesirable possibility that the tabs will tear off of the bandage. In fact, this is presented as a feature of that invention, which is drawn to a more permanent bandage. The perforations of that invention also eliminate the possibility of the strips into a roll formation, with perforations between the strips to separate them from the rest of the roll. This is an important limitation, as a roll formation is particularly easy to use in a hospital or a similar setting where these tapes are used in large quantity (e.g., blood donation facilities). The roll eliminates the necessity for the gloved practitioner to remove individual packaging or a shield from each tape used.

One partial solution to this problem is to fold the end of the tape roll under onto itself, creating a non-adhesive tab. However, this maneuver, too, is difficult with a gloved hand, it must be repeated every time a piece of tape is used, and it creates only one tab end on each tape. In certain circumstances, it may be desirable to remove a tape by pulling in one direction particularly; however, with only one tape, the direction must be determined ahead of time, and the tape applied in the appropriate orientation for later removal.

SUMMARY OF THE INVENTION

This invention is a new style of bandage, or tape for securing a bandage, which is easy to remove from a roll and from the skin by someone who is wearing gloves. The presence of permanently attached, non-adhesive tabs at both ends of a predetermined length of tape allows the tape to be easily removed by a medical practitioner who is wearing gloves, or by a patient who does not have the dexterity to peel a regular tape or bandage off the skin. The tapes may be stored in and dispensed from a roll, by separating the strips with perforated areas to allow for removal from the remainder of the roll, or in a pad.

It is therefore an object of this invention to provide a style of surgical or bandage tape which is easily removed from the skin or from a roll or pad of similar tapes by someone wearing gloves.

It is a further object of this invention to provide a temporary tape or bandage which may be easily removed from the skin by a patient with limited dexterity.

It is yet a further object of the invention to provide a system for packaging tapes or bandages of a predetermined lengths, with non-adhesive areas at each end, such that the tapes or bandages are easily removed from said packaging by one who is wearing gloves.

These and other objectives, features, and advantages of the present invention may be found in the following description, drawings, and claims.

DETAILED DESCRIPTION OF THE INVENTION

Figure 1:
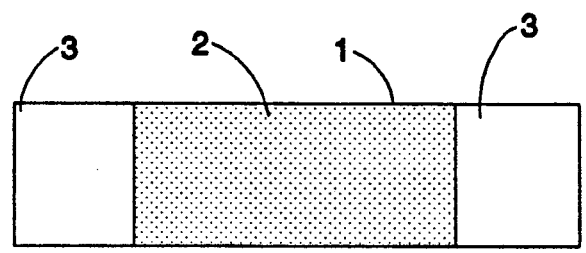
FIG. 1 is a bottom (adhesive side) view of a single tape with non-adhesive ends.
Figure 4:
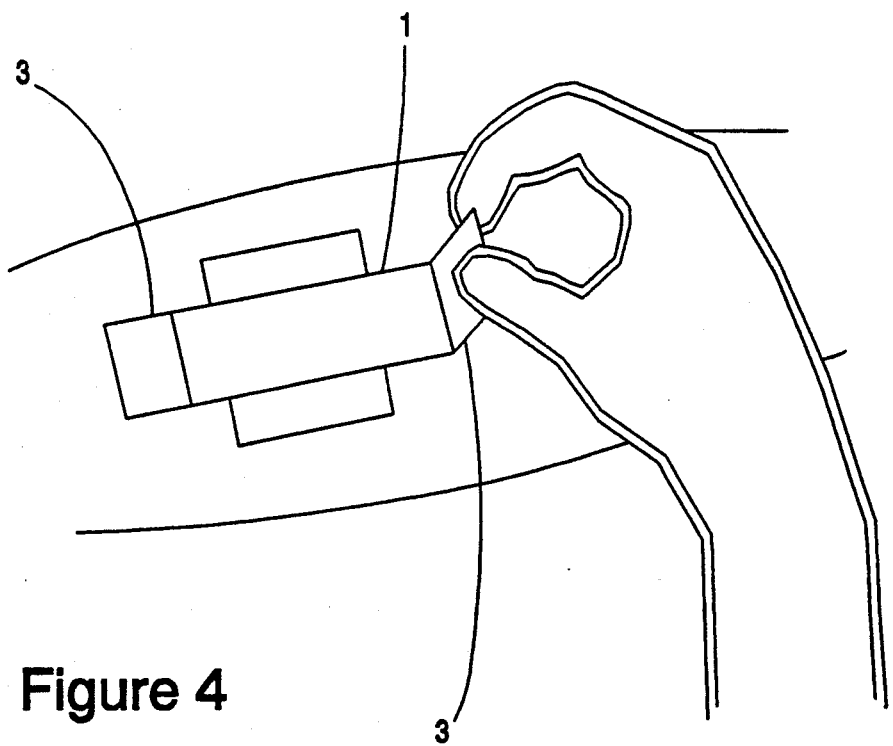
FIG. 4 shows the tape of the present invention in place on a patient's arm, and demonstrates removal of such tape from the skin by a gloved hand.

This invention is a new style of tape which is easily handled by those wearing gloves. It has a middle section (1) with adhesive on one surface (2), and two end sections (3) having no adhesive on either surface (see FIG. 1). One end section is fixedly attached to each end of the middle section. The tape may be of any length or width, may be made of any material which is sufficiently flexible to conform to the contours of the human body, e.g., rubber, cloth, paper, or flexible plastic, and may be packaged individually or in a roll or pad formation. The end sections (3) should be long enough that they may be gripped by a gloved hand, as shown in FIG. 4, without the glove coming into contact with the middle section (1) of the tape.

Figure 2:
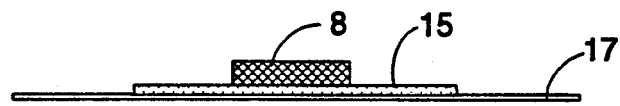
FIG. 2 is a side view of a single bandage with non-adhesive ends, made by applying adhesive to one portion of a non-adhesive tape, and applying an absorbant pad to the adhesive section.
Figure 3:
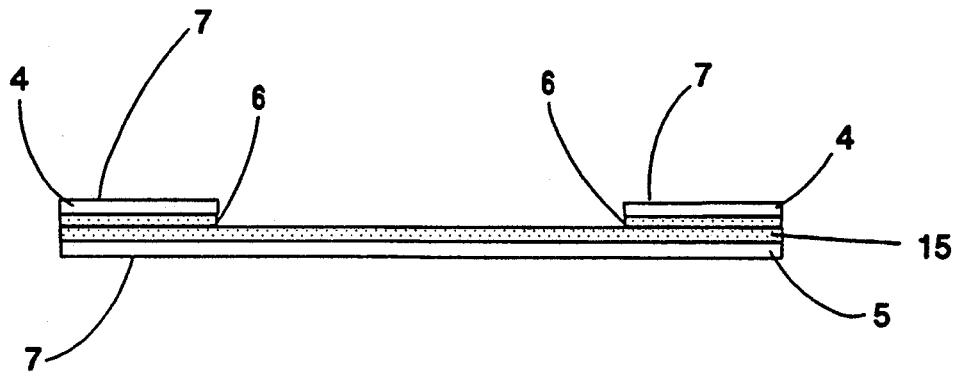
FIG. 3 is a side view of a single tape with non-adhesive ends, made by joining a piece of tape to separate tab pieces.

The tape may be made in many ways. A single tape may be made by applying adhesive (15) to only one portion of a piece of nonadhesive tape (17), as in FIG. 2, or by applying short tab pieces (4) of backing material to the ends of a longer piece of tape (5) which has adhesive (15) on one side (FIG. 3). The backing material may be non-adhesive material, or material which is adhesive on one side. If an adhesive material is desired, the same tape that is used for the long piece may also be used as a backing material, or a different material may be selected. If such adhesive material is used, it is placed onto the main tape (5) such that the adhesive sides of the tape and the backing material come together (6), creating non-adhesive outer surfaces (7) on both sides. The use of adhesive backing material for the tabs creates a firmer bond between the adhesive surfaces of the tape and the tabs, with less likelihood that the backing material will become separated from the tape, which would defeat the purpose of the tabs.

A bandage may be made by applying an absorbent pad (8) (made of gauze, cloth, or any absorbent material) to a tape made by any of the methods outlined above, or by joining such a pad between two pieces of tape that each have a single non-adhesive end, such that these non-adhesive ends are distal to the pad.

Figure 5:
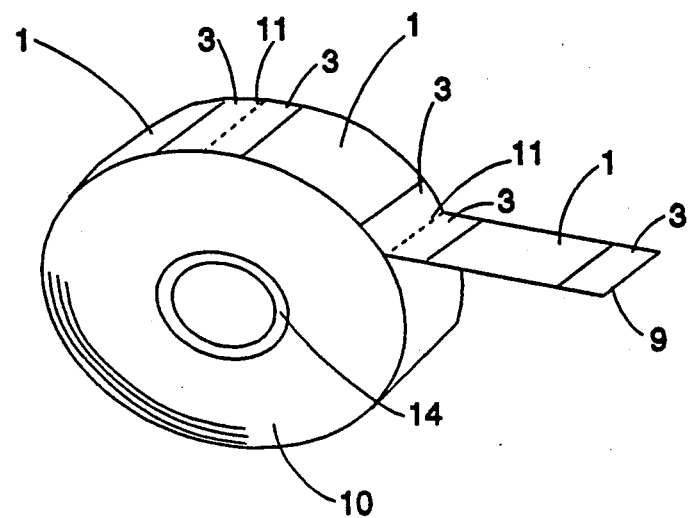
FIG. 5 shows a roll of tape as disclosed herein.

The tapes may also be individually packaged or placed into a roll, with the individual pieces separated from each other by perforations for easy removal from the roll. See FIG. 5. The free end (9) of the roll (10) will have a non-adhesive tab (3) which may be gripped to pull the next tape from the roll. The tape may be removed from the roll by a sharp tug, which will tear the tape at the perforations (11). This procedure may be performed with or without gloves, and the tape will not stick to the gloves.

Figure 6:
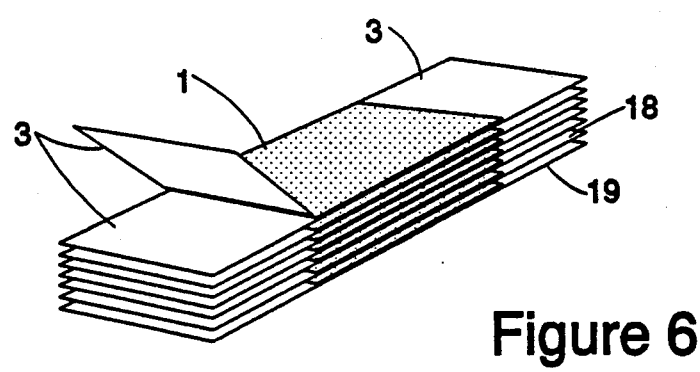
FIG. 6 shows a pad of tapes.

The tapes may also be packaged in a pad formation, as shown in FIG. 6, wherein the adhesive side of each tape is attached to the non-adhesive side of the tape below it. The bottom-most tape (18) may be placed onto a heavy backing material (19), such as cardboard. The non-adhesive tabs allow the tapes to be removed from the pad for individual use.

A roll of the tapes may be made by a manufacturing process whereby a length of tape of the desired width is fed along a path, with the adhesive side down and the non-adhesive side up, and a length of backing material is fed in a path perpendicular to and underneath the first length. If the backing material has an adhesive side, it must be fed with the adhesive side up and the non-adhesive side down. The tape is advanced along its path to the desired length, the tape and the backing material are brought together, and a sharp blade is used to cut the backing material at the edges of the tape, creating an area on the tape which has backing attached. If an adhesive backing is used, this area will have adhesive in the middle, between the two materials, but none on either exposed surface. A perforating device can then be used to perforate the tape and backing in the center of this nonadhesive area. The tape, with non-adhesive sections (provided by the backing material) and perforations, can then be wound onto a roll (14).

By grasping the non-adhesive tab at either end of the tape (see FIG. 4), one may easily remove the tape from the roll or pad, and later from the skin of a patient, even when wearing gloves.

The foregoing description has been directed to particular embodiments of the invention in accordance with the requirements of the Patent Statutes for the purposes of illustration and explanation. It will be apparent, however, to those skilled in this art that many modifications and changes will be possible without departure from the scope and spirit of the invention. It is intended that the following claims be interpreted to embrace all such modifications.

What is claimed is:

1. A roll of tapes with non-adhesive ends which may be used by a gloved person, comprising:
   a) a center spool,
   b) a length of tope wound around said spool, said tape comprising repeating segments, each of said segments comprising:
      1) a first non-adhesive section, having anon-adhesive surfaces on both sides thereof,
      2) a second non-adhesive section, having non-adhesive surfaces on both sides thereof, and
      3) an adhesive section, having an adhesive surface on one side thereof and a non-adhesive surface on the other side thereof, disposed between said first non-adhesive section and said second non-adhesive section, such that said adhesive surface covers the entire area on said one side of said segment between said first non-adhesive section and said second non-adhesive section, and does not contain any nonadhesive areas, and is permanently attached to said first and second non-adhesive sections, whereby each of said repeating segments is attached to at lest one other of said repeating segments, in an end-to-end manner, with a perforated attachment between segments.

2. The roll of claim 1, wherein the non-adhesive sections of each of said segments are of sufficient size to enable said gloved person to grasp one of said non-adhesive sections using a hand covered by a glove, without having said glove come into contact with the adhesive surface of the adhesive section of said segment.

* * * * *